(12) United States Patent
Birner et al.

(10) Patent No.: US 8,273,686 B2
(45) Date of Patent: Sep. 25, 2012

(54) METHOD FOR COMBATING PHYTOPATHOGENIC FUNGI

(75) Inventors: Erich Birner, Altleiningen (DE); Luis Carlos Mateo Garcia, Barcelona (ES)

(73) Assignee: BASF SE, Ludwigshafen (DE)

( * ) Notice: Subject to any disclaimer, the term of this patent is extended or adjusted under 35 U.S.C. 154(b) by 882 days.

(21) Appl. No.: 12/293,686

(22) PCT Filed: Mar. 20, 2007

(86) PCT No.: PCT/EP2007/052643
§ 371 (c)(1),
(2), (4) Date: Sep. 19, 2008

(87) PCT Pub. No.: WO2007/110354
PCT Pub. Date: Oct. 4, 2007

(65) Prior Publication Data
US 2010/0292237 A1  Nov. 18, 2010

(30) Foreign Application Priority Data
Mar. 24, 2006  (EP) .................................... 06111704

(51) Int. Cl.
*A01N 55/02* (2006.01)
*A01N 57/00* (2006.01)
*A01N 43/40* (2006.01)
*A01N 43/60* (2006.01)
*A01N 43/36* (2006.01)
*A01N 43/84* (2006.01)
*A01N 43/54* (2006.01)
*A01N 43/56* (2006.01)

(52) U.S. Cl. ........ 504/126; 504/128; 504/130; 504/136; 504/138; 504/190; 504/224; 504/243; 504/282; 504/286

(58) Field of Classification Search .................. None
See application file for complete search history.

(56) References Cited

U.S. PATENT DOCUMENTS

| | | | |
|---|---|---|---|
| 4,829,085 A | 5/1989 | Wenderoth et al. |
| 4,937,372 A | 6/1990 | Wenderoth et al. |
| 5,157,037 A | 10/1992 | Schuetz et al. |
| 5,194,662 A | 3/1993 | Brand et al. |
| 5,395,854 A | 3/1995 | Brand et al. |
| 5,534,550 A | 7/1996 | Gerdes et al. |
| 5,723,471 A | 3/1998 | De Fraine et al. |
| 5,756,426 A | 5/1998 | Ziegler et al. |
| 5,824,705 A | 10/1998 | Müeller et al. |
| 5,869,517 A | 2/1999 | Muller et al. |
| 5,874,467 A | 2/1999 | Bayer et al. |
| 5,889,059 A | 3/1999 | Bayer et al. |
| 5,948,932 A | 9/1999 | Grote et al. |
| 6,103,717 A | 8/2000 | Heinemann et al. |
| 6,407,100 B1 | 6/2002 | Isenring et al. |
| 6,566,547 B1 | 5/2003 | Bushell et al. |
| 2001/0006964 A1 | 7/2001 | Dehne et al. |
| 2003/0130119 A1 | 7/2003 | Watrin |
| 2004/0259732 A1 | 12/2004 | Asrar et al. |
| 2005/0043176 A1 | 2/2005 | Forster |
| 2005/0065031 A1 | 3/2005 | Forster |
| 2005/0085389 A1 | 4/2005 | Forster et al. |
| 2005/0124815 A1 | 6/2005 | Elbe et al. |
| 2005/0198896 A1 | 9/2005 | Quaghebeur |
| 2010/0105669 A1 | 4/2010 | Voeste et al. |

FOREIGN PATENT DOCUMENTS

| | | |
|---|---|---|
| CA | 2409649 | 11/2001 |
| CA | 2457570 | 2/2003 |
| CA | 2478591 | 9/2003 |
| CA | 2 570 497 | 12/2005 |
| CN | 1565182 | 1/2005 |
| CN | 1565183 | 1/2005 |
| DE | 4437945 | 4/1995 |
| DE | 10241611 | 12/2003 |
| EP | 0 178 826 | 4/1986 |
| EP | 0 253 213 | 1/1988 |
| EP | 0 254 426 | 1/1988 |
| EP | 0 278 595 | 8/1988 |
| EP | 0 280 185 | 8/1988 |
| EP | O 398 692 | 1/1989 |
| EP | 0 350 691 | 1/1990 |
| EP | O 382 375 | 8/1990 |
| EP | 0 398 692 | 11/1990 |
| EP | 0 460 575 | 12/1991 |
| EP | 0 463 488 | 1/1992 |
| EP | 0 477 631 | 4/1992 |
| EP | 0 628 540 | 12/1994 |
| EP | 1 606999 | 12/2005 |
| WO | WO 93/15046 | 8/1993 |
| WO | WO 95/18789 | 7/1995 |
| WO | WO 95/21153 | 8/1995 |
| WO | WO 95/21154 | 8/1995 |
| WO | WO 95/24396 | 9/1995 |

(Continued)

OTHER PUBLICATIONS

Groenewald et al. (Screening Phaeoacremonium against twelve fungicides to determine base line sensitivity, South African J. Science, vol. 97, 2001, pp. XIV-XV).*

Jaspers et al. (Effects of fungicides, in vitro, on germination and growth of *Phaeomoniella chlamydospora*, Phytopathologica Mediterranea, vol. 40 no. suppl., 2001, pp. S453-S458).*

Use of triazole fungicides on woody plants, Research Disclosure, Mason Publications, Hampshire, GB, vol. 496, No. 6, 2005, pp. 1-2.*

Anonymous, "Use of Triazole Fungicides on Woody Plants", Research Disclosure, Mason Publications, Aug. 2005, 3 pages, vol. 496, No. 6, Search Report.

Bartlett, Dave W. et al., "Review The Strobilurin fungicides", Pest Manag Sci., 2002, p. 649-662, vol. 58, Search Report.

(Continued)

*Primary Examiner* — Alton Pryor
(74) *Attorney, Agent, or Firm* — Brinks Hofer Gilson & Lione

(57) ABSTRACT

The present invention relates to the use of an active compound that inhibits the mitochondrial breathing chain at the level of the b/$c_1$ complex for combating phytopathogenic fungi.

7 Claims, No Drawings

FOREIGN PATENT DOCUMENTS

| WO | WO 96/01256 | 1/1996 |
|---|---|---|
| WO | WO 97/01277 | 1/1997 |
| WO | WO 97/05103 | 2/1997 |
| WO | WO 97 /06133 | 2/1997 |
| WO | WO 97/15552 | 5/1997 |
| WO | WO 97/27189 | 7/1997 |
| WO | WO 98/29537 | 7/1998 |
| WO | WO 01/82701 | 11/2001 |
| WO | WO 03/045146 | 6/2003 |
| WO | WO 03/045147 | 6/2003 |
| WO | WO 03/045150 | 6/2003 |
| WO | WO 03/066610 | 8/2003 |
| WO | WO 03/075663 | 9/2003 |
| WO | WO 2005/094155 | 10/2005 |
| WO | WO 2007/048735 | 5/2007 |
| WO | WO 2007048735 | 5/2007 |
| WO | WO 2007/104658 | 9/2007 |
| WO | WO 2007/104660 | 9/2007 |
| WO | WO 2007/104677 | 9/2007 |
| WO | WO 2009/003953 | 1/2009 |

OTHER PUBLICATIONS

Cough, J.M., "The Strobilurins, Oudemansins and Myxothiazols, Fungicidal Derivatives of β-Methoxyacrylic Acid", Natural Product Reports, 1993, p. 565-574, vol. 10, No. 6.

Groenewald, M., et al. "Screening *Phaeoacremonium chlamydosporum* against twelve fungicides to determine base-line sensitivity", South African Journal of Science, 2001, p. XIV-XV, vol. 97, Search Report.

Jaspers, Marlene V., "Effect of fungicides, in vitro, on germination and growth of *Phaeomoniella chlamydospora*" Phytopathol. Mediterr., 2001, p. S453-S458, vol. 40, Search Report.

Mugnai, L., et al., "Esca (Black Measles) and Brown Wood-Streaking: Two Old and Elusive Diseases of Grapevines", Plant Disease, American Phytopathological Society, May 1999, p. 404-418, vol. 83, No. 5, Search Report.

Roehl, Franz, et al., "Species dependence of mitochondrial respiration inhibition by strobilurin analogues", Biochemical Society Transactions, 1993, p. 63S, vol. 22.

International Search Report, completed Aug. 22, 2007, in corresponding International Application No. PCT/EP2007/052643, filed Mar. 20, 2007.

International Preliminary Report on Patentability dated Sep. 30, 2008, as prepared in corresponding International Application No. PCT/EP2007/052643, filed Mar. 20, 2007.

Santos, Conceicao et al., "Response of Vitis vinifera L. plants inoculated with *Phaeoacremonium angustius* and *Phaeomoniella chlamydospora* to thiabendazole, resveratrol and sodium arsenite", Scientia Horticulturae, 2006, p. 131-136 vol. 107, Search Report.

Gulnaz, A., et al., "Seed treatment with growth regulators and crop productivity. I. 2,4/D as an inducer of salinioty—tolerance in wheat (*Triticum aestivumm* L.)", Plant and Soil,, 1999, vol. 210, pp. 209/ 217.

Sobolewski Jet al., "New fungicides used for complex control of diseases on tomato growing in the filed and in the greenhDuse", Process in Plant Protection, (2002) vol. 42, No. 2, lop. 790/792. (Abstract) XP002241579.

Bartlett, Dave W., et al. "Review The Strobilurin Fungicides", Pest Manag Sci., 2002, p. 649-662, vol. 58.

Grossmann et al., "Bioregulatory Effects of the Fungicidal Strobilurin Kresoxim-Methyl in Wheat (*Triticum aestivum*)," Pestic Sci., vol. 50, (1997), pp. 11-20. XP-002462418.

Herms, Stefan, et al. "A Strobiluin Fungicide Enhances the Resistanec of Tobacco against Tobacco Mosaic Virus and *Pseudomonas Syringae* pv *tabaci*"., Plant Physiology, Sep. 2002, pp. 120-127, vol. 130.

Jabs et al., "Anti-Oxidative and Anti-Senescence Effects of the Strobilurin Pyraclostrobin in Plants: A New Strategy to Cope with Environmental Stress in Cereals," BCPC Conference—Pests & Diseases, vol. 2, (2002), pp. 941-946. XP-002462420.

Jaspers, Marlene V., "Effect of fungicides, in vitro on germination and growth of *Phaeomoniella chlmydospora*", Phytopathol. Mediterr. 2001, p. S453-S458, vol. 40, supplement.

Lalk et al., "Hardening, Absicisic Acid, Proline and Freezing Resistance in Two Winter Wheat Varieties," Physiol. Plant, vol. 63, (1985), pp. 287-292.

Pasquer, Frederique et al., "Specific patterns of changed in wheat gene expression after treatment with three antifungal compounds"., Plan Molecular Biology, 2005, p. 693-707, vol. 57.

Reade et al., "Can Picoxystrobin Protect Winter Wheat from Environmental Stress?" Congress Proceedings—BCPC International Contress: Crop Science & Technology, Glasgow, UK, vol. 2, (Nov. 10-12, 2003), pp. 863-868. XP-002462421.

Rucklidge, Garry J., "Cell-Adhesion molecules and metalloproteinases: a linked role in tumour cell invasiveness"., Biocehm. Soc. Trans., 22, 63S, 1994.

Stierl, R., et al., "Activity of the new BASF Strobilurin fungicides, BAS 500 F, against *Septoria tritici* on wheat", STN-International and BCPC Conference—Pests & Diseases, vol. 3, 2000, pp. 859-864.

Stierl, R., et al., "Activity of the new BASF Strobilurin fungicide, BAS 500 F, against *Plasmopara viticola* on grapes", STN-International and BCPC Conference—Pests & Diseases, vol. 1, 2000, pp. 261-266.

Venancio, W. C., et al., "Physiological Effects of Strobilurin fungicides on Plants", Publ. UEPG Ci. Exatas Terra, Ci. Agr. Eng., Ponta Grossa, 2003, p. 59-68, vol. 9, No. 3.

* cited by examiner

METHOD FOR COMBATING PHYTOPATHOGENIC FUNGI

This application is a National Stage application of International Application No. PCT/EP2007/052643 filed Mar. 20, 2007, the entire contents of which is hereby incorporated herein by reference. This application also claims the benefit under 35 U.S.C. §119 of European Patent Application No. 06111704.0 filed Mar. 24, 2006 the entire contents of which is hereby incorporated herein by reference.

The present invention relates to the use of an active compound that inhibits the mitochondrial breathing chain at the level of the $b/c_1$ complex for combating Esca.

Since a few years, winegrowers are confronted with the severe incidence of the Esca disease causing serious damages of the vinegrapes and resulting in considerable harvest and yield losses.

Esca stands for a complex of fungi pathogens. The pathogens that can be associated with Esca symptoms according to the literature are *Fomitiporia punctata* (syn. *Phellinus punctatus*), *Fomitiporia mediterrana*, *Phaeroacremonium* spp.: *Phaeroacremonium aleophilum* and *Phaemoniella chlamydosporum*. One particular fungus, which was isolated from the wood of Esca attacked grapevines, is *Phaemoniella chlamydosporum* (white rot fungi).

There is known an acute form and a chronic form of the Esca disease and Esca can lead to different symptoms. The symptoms of the chronic form of the Esca disease are, for example, light green spots on the leaves and dark blotches on the berries. Further, the woody parts inside the vinegrapes often transform into a soft and spongy material, which is mostly observed in older vinegrapes. A vinegrape suffering from the acute form of Esca abruptly begins to welt and ultimately withers and dies.

There does not exist any effective treatment against Esca up to now. Although sodium arsenates have proven effective against Esca, sodium arsenates are environmentally and toxicologically questionable and are, therefore, prohibited in most of the countries. Thus, at the moment, the only way to eliminate Esca in contaminated vinegrapes and to prevent a spreading of the disease is the removing and burning of contaminated vines, back cutting of the vines in order to achieve a renewal of the vines and the like. Further, it is recommended to the vinegrowers to perform a late vine pruning in order to keep the time period for a potential infection with the Esca pathogens as short as possible. There do not exist any direct measures for controlling or combating Esca.

Consequently, there exists a strong need for an effective means against the Esca disease.

Surprisingly, it has now been found that active compounds that inhibit the mitochondrial breathing chain at the level of the $b/c_1$ complex can effectively be used for combating Esca, particularly in vines. Therefore, the present invention is directed to the use of an active compound that inhibits the mitochondrial breathing chain at the level of the $b/c_1$ complex for combating Esca. Furthermore, the present invention relates to the use of an active compound that inhibits the mitochondrial breathing chain at the level of the $b/c_1$ complex together with at least one further active compound against Esca, particularly to the use of a composition comprising at least one active compound that inhibits the mitochondrial breathing chain at the level of the $b/c_1$ complex together with one or more further fungicidal compounds. The present invention also provides a method for combating Esca, which comprises treating the fungi, their habitat, the plants, the soil and/or materials to be kept free therefrom with an effective amount of an active compound that inhibits the mitochondrial breathing chain at the level of the $b/c_1$ complex, wherein said active compound can also be used together with at least one further active ingredient.

Active compounds that inhibit the mitochondrial breathing chain at the level of the $b/c_1$ complex are known as fungicides from the literature [see for example Dechema-Monographien Bd. 129, 27-38, VCH Verlagsgemeinschaft Weinheim 1993; Natural Product Reports 1993, 565-574; Biochem. Soc. Trans. 22, 63S (1993)]. However, there has been no suggestion to date that such active compounds can effectively be used for controlling Esca, which has only been found within the framework of the present invention.

A particularly important class of active compounds that inhibit the mitochondrial breathing chain at the level of the $b/c_1$ complex are strobilurins. Strobilurins are generally known as fungicides since a long time and have, in some cases, also been described as insecticides (EP-A 178 826; EP-A 253 213; WO 93/15046; WO 95/18789; WO 95/21153; WO 95/21154; WO 95/24396; WO 96/01256; WO 97/15552; WO 97/27189). A further example of an active compounds that inhibits the mitochondrial breathing chain at the level of the $b/c_1$ complex is famoxadone (5-methyl-5-(4-phenoxyphenyl)-3-(phenylamino)-2,4-oxazolidinedione).

In a preferred embodiment of the present invention, strobilurins are used against Esca. According to the present invention, strobilurins which have proven particularly suitable for controlling or combating Esca are selected from 1) compounds of formula I

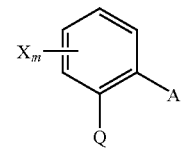

in which

X is halogen, $C_1$-$C_4$-alkyl or trifluoromethyl;

m is 0 or 1;

Q is C(=CH—CH$_3$)—COOCH$_3$, C(=CH—OCH$_3$)—COOCH$_3$, C(=N—OCH$_3$)—CONHCH$_3$, C(=N—OCH$_3$)—COOCH$_3$, N(—OCH$_3$)—COOCH$_3$, or a group Q1

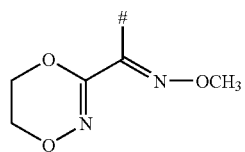

wherein # denotes the bond to the phenyl ring;

A is —O—B, —CH$_2$O—B, —OCH$_2$—B, —CH$_2$S—B, —CH=CH—B, —CH$_2$O—N=C(R$^1$)—B, —CH$_2$S—N=C(R$^1$)—B, —CH$_2$O—N=C(R$^1$)—CH=CH—B, or —CH$_2$O—N=C(R$^1$)—C(R$^2$)=N—OR$^3$, where B is phenyl, naphthyl, 5-membered or 6-membered heteroaryl or 5-membered or 6-membered heterocyclyl, containing one, two or three N atoms and/or one O or S atom or one or two O and/or S atoms, the ring systems being unsubstituted or substituted by one, two or three radicals R$^a$:

$R^a$ is independently cyano, nitro, amino, aminocarbonyl, aminothiocarbonyl, halogen, $C_1$-$C_6$-alkyl, $C_1$-$C_6$-haloalkyl, $C_1$-$C_6$-alkylcarbonyl, $C_1$-$C_6$-alkylsulfonyl, $C_3$-$C_6$-cycloalkyl, $C_1$-$C_6$-alkoxy, $C_1$-$C_6$-haloalkoxy, $C_1$-$C_6$-alkyloxycarbonyl, $C_1$-$C_6$-alkylthio, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylaminothiocarbonyl, di-$C_1$-$C_6$-alkylaminothiocarbonyl, $C_2$-$C_6$-alkenyl, $C_2$-$C_6$-alkenyloxy, phenyl, phenoxy, benzyl, benzyloxy, 5- or 6-membered heterocyclyl, 5- or 6-membered heteroaryl, 5- or 6-membered heteroaryloxy, $C(=NOR^a)$—$R^b$ or $OC(R^a)_2$—$C(R^b)=NOR^b$, the cyclic radicals, in turn, being unsubstituted or substituted by one, two or three radicals $R^b$:

$R^b$ is independently cyano, nitro, halogen, amino, aminocarbonyl, aminothiocarbonyl, $C_1$-$C_6$-alkyl, $C_1$-$C_6$-haloalkyl, $C_1$-$C_6$-alkylsulfonyl, $C_1$-$C_6$-alkylsulfinyl, $C_3$-$C_6$-cycloalkyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylaminothiocarbonyl, di-$C_1$-$C_6$-alkyl-aminothiocarbonyl, $C_2$-$C_6$-alkenyl, $C_2$-$C_6$-alkenyloxy, $C_3$-$C_6$-cycloalkyl, $C_3$-$C_6$-cycloalkenyl, phenyl, phenoxy, phenylthio, benzyl, benzyloxy, 5- or 6-membered heterocyclyl, 5- or 6-membered heteroaryl, 5- or 6-membered heteroaryloxy or $C(=NOR^A)$—$R^B$;

$R^A$, $R^B$ are independently hydrogen or $C_1$-$C_6$-alkyl;

$R^1$ is hydrogen, cyano, $C_1$-$C_4$-alkyl, $C_1$-$C_4$-haloalkyl, $C_3$-$C_6$-cycloalkyl, $C_1$-$C_4$-alkoxy, or $C_1$-$C_4$-alkylthio;

$R^2$ is phenyl, phenylcarbonyl, phenylsulfonyl, 5- or 6-membered heteroaryl, 5- or 6-membered heteroarylcarbonyl or 5- or 6-membered heteroarylsulfonyl, the ring systems being unsubstituted or substituted by one, two or three radicals $R^a$, $C_1$-$C_{10}$-alkyl, $C_3$-$C_6$-cycloalkyl, $C_2$-$C_{10}$-alkenyl, $C_2$-$C_{10}$-alkynyl, $C_1$-$C_{10}$-alkylcarbonyl, $C_2$-$C_{10}$-alkenylcarbonyl, $C_3$-$C_{10}$-alkynylcarbonyl, $C_1$-$C_{10}$-alkylsulfonyl, or $C(=NOR^a)$—$R^b$, the hydrocarbon radicals of these groups being unsubstituted or substituted by one, two or three radicals $R^c$:

$R^c$ is independently cyano, nitro, amino, aminocarbonyl, aminothiocarbonyl, halogen, $C_1$-$C_6$-alkyl, $C_1$-$C_6$-haloalkyl, $C_1$-$C_6$-alkylsulfonyl, $C_1$-$C_6$-alkylsulfinyl, $C_1$-$C_6$-alkoxy, $C_1$-$C_6$-haloalkoxy, $C_1$-$C_6$-alkoxycarbonyl, $C_1$-$C_6$-alkylthio, di-$C_1$-$C_6$-alkylamino, $C_1$-$C_6$-alkylaminocarbonyl, di-$C_1$-$C_6$-alkylaminocarbonyl, $C_1$-$C_6$-alkylaminothiocarbonyl, di-$C_1$-$C_6$-alkylaminothiocarbonyl, $C_2$-$C_6$-alkenyl, $C_2$-$C_6$-alkenyloxy, $C_3$-$C_6$-cycloalkyl, $C_3$-$C_6$-cycloalkyloxy, 5- or 6-membered heterocyclyl, 5- or 6-membered heterocyclyloxy, benzyl, benzyloxy, phenyl, phenoxy, phenylthio, 5- or 6-membered heteroaryl, 5- or 6-membered heteroaryloxy and heteroarylthio, it being possible for the cyclic groups, in turn, to be partially or fully halogenated or to have attached to them one, two or three radicals $R^a$; and $R^3$ is hydrogen, $C_1$-$C_6$-alkyl, $C_2$-$C_6$-alkenyl, $C_2$-$C_6$-alkynyl, the hydrocarbon radicals of these groups being unsubstituted or substituted by one, two or three radicals $R^c$; and 2) the strobilurins (2-chloro-5-[1-(3-methyl-benzyloxyimino)-ethyl]-benzyl)-carbamic acid methyl ester, (2-chloro-5-[1-(6-methyl-pyridine-2-ylmethoxyimino)-ethyl]-benzyl)-carbamic acid methyl ester, 2-(ortho-((2,5-dimethylphenyl-oxymethylene)phenyl)-3-methoxy-acrylic acid methyl ester, 2-(2-(6-(3-chloro-2-methyl-phenoxy)-5-fluoropyrimidin-4-yloxy)-phenyl)-2-methoxyimino-N-methyl-acetamide, and 3-methoxy-2-(2-(N-(4-methoxy-phenyl)-cyclopropanecarboximidoylsulfanylmethyl)-phenyl)-acrylic acid methyl ester.

Compounds of formula I are generally known as fungicides since a long time (see references above).

The publications cited above describe synthesis routes for the preparation of strobilurins used in the method according to the invention, the disclosure of which is hereby incorporated.

In one embodiment of the present invention strobilurines of formula I are used.

In another embodiment of the present invention a strobilurin compound selected from (2-chloro-5-[1-(3-methyl-benzyloxyimino)-ethyl]-benzyl)-carbamic acid methyl ester, (2-chloro-5-[1-(6-methyl-pyridine-2-ylmethoxyimino)-ethyl]-benzyl)-carbamic acid methyl ester and 2-(ortho-((2,5-dimethylphenyl-oxymethylene)phenyl)-3-methoxy-acrylic acid methyl ester is used.

Especially preferred for the methods according to the invention are strobilurins with the following meanings of the substituents, in each case alone or in combination, the disclosure of the publications cited being hereby incorporated:

In one preferred embodiment of the present invention, preferred strobilurins of formula I wherein Q is $N(—OCH_3)$—$COOCH_3$ are the compounds described in the publications WO 93/15046 and WO 96/01256.

In another preferred embodiment of the present invention, preferred strobilurins of formula I, wherein Q is $C(=CH—OCH_3)$—$COOCH_3$ are the compounds described in the publications EP-A 178 826 and EP-A 278 595.

In another preferred embodiment of the present invention, preferred strobilurins of formula I, wherein Q is $C(=N—OCH_3)$—$COOCH_3$ are the compounds described in the publications EP-A 253 213 and EP-A 254 426.

In another preferred embodiment of the present invention, preferred strobilurins of formula I, wherein Q is $C(=N—OCH_3)$—$CONHCH_3$ are the compounds described in the publications EP-A 398 692, EP-A 477 631 and EP-A 628 540.

In another preferred embodiment of the present invention, preferred strobilurins of formula I, wherein Q is $C(=CH—CH_3)$—$COOCH_3$ are the compounds described in the publications EP-A 280 185 and EP-A 350 691.

In another preferred embodiment of the present invention, preferred strobilurins of formula I, wherein Q is —$CH_2O$—$N=C(R^1)$—B are the compounds described in the publications EP-A 460 575 and EP-A 463 488.

In another preferred embodiment of the present invention, preferred strobilurins of formula I, wherein A is —O—B are the compounds described in the publications EP-A 382 375 and EP-A 398 692.

In another preferred embodiment of the present invention, preferred strobilurins of formula I, wherein A is —$CH_2O$—$N=C(R^1)$—$C(R^2)=N$—$OR^3$ are the compounds described in the publications WO 95/18789, WO 95/21153, WO 95/21154, WO 97/05103 and WO 97/06133.

Especially preferred are the strobilurins of the formula I in which

Q is $N(—OCH_3)$—$COOCH_3$,
A is $CH_2$—O— and
B is 3-pyrazolyl or 1,2,4-triazolyl, where B has attached to it one or two substituents selected from the group of
halogen, methyl and trifluoromethyl and
phenyl and pyridyl, in particular 2-pyridyl, substituted by 1 to 3 radicals $R^b$.

These active ingredients are described by formula II,

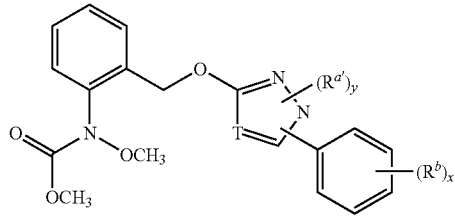

in which T is a carbon or a nitrogen atom, $R^{a'}$ is independently selected from halogen, methyl and trifluoromethyl, y is zero, 1 or 2, $R^b$ is as defined for formula I, x is zero, 1, 2, 3 or 4.

More preferred active ingredients are those of formula II':

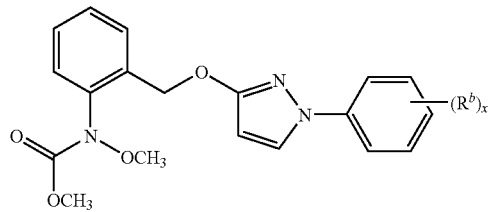

in which $R^b$ is as defined for formula I.

According to the present invention, the strobilurin is especially preferably selected from the compounds listed in the following tables.

TABLE 1

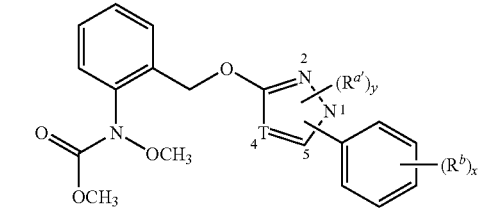

II

| No. | T | $(R^{a'})_y$ | Position of the group phenyl-$(R^b)_x$ | $(R^b)_x$ | Reference |
|---|---|---|---|---|---|
| II-1 | N | — | 1 | 2,4-Cl$_2$ | WO 96/01256 |
| II-2 | N | — | 1 | 4-Cl | WO 96/01256 |
| II-3 | CH | — | 1 | 2-Cl | WO 96/01256 |
| II-4 | CH | — | 1 | 3-Cl | WO 96/01256 |
| II-5 | CH | — | 1 | 4-Cl | WO 96/01256 |
| II-6 | CH | — | 1 | 4-CH$_3$ | WO 96/01256 |
| II-7 | CH | — | 1 | H | WO 96/01256 |
| II-8 | CH | — | 1 | 3-CH$_3$ | WO 96/01256 |
| II-9 | CH | 5-CH$_3$ | 1 | 3-CF$_3$ | WO 96/01256 |
| II-10 | CH | 1-CH$_3$ | 5 | 3-CF$_3$ | WO 99/33812 |
| II-11 | CH | 1-CH$_3$ | 5 | 4-Cl | WO 99/33812 |
| II-12 | CH | 1-CH$_3$ | 5 | — | WO 99/33812 |

TABLE 2

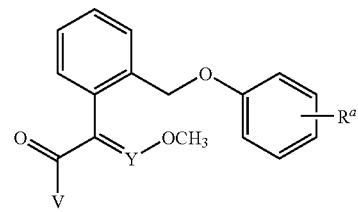

III

| No. | V | Y | $R^a$ | Reference |
|---|---|---|---|---|
| III-1 | OCH$_3$ | N | 2-CH$_3$ | EP-A 253 213 |
| III-2 | OCH$_3$ | N | 2,5-(CH$_3$)$_2$ | EP-A 253 213 |
| III-3 | NHCH$_3$ | N | 2,5-(CH$_3$)$_2$ | EP-A 477 631 |
| III-4 | NHCH$_3$ | N | 2-Cl | EP-A 398 692 |
| III-5 | NHCH$_3$ | N | 2-CH$_3$ | EP-A 398 692 |
| III-6 | NHCH$_3$ | N | 2-CH$_3$, 4-OCF$_3$ | EP-A 628 540 |
| III-7 | NHCH$_3$ | N | 2-Cl, 4-OCF$_3$ | EP-A 628 540 |
| III-8 | NHCH$_3$ | N | 2-CH$_3$, 4-OCH(CH$_3$)—C(CH$_3$)=NOCH$_3$ | EP-A 11 18 609 |
| III-9 | NHCH$_3$ | N | 2-Cl, 4-OCH(CH$_3$)—C(CH$_3$)=NOCH$_3$ | EP-A 11 18 609 |
| III-10 | NHCH$_3$ | N | 2-CH$_3$, 4-OCH(CH$_3$)—C(CH$_2$CH$_3$)=NOCH$_3$ | EP-A 11 18 609 |
| III-11 | OCH$_3$ | CH | 2,5-(CH$_3$)$_2$ | EP-A 226 917 |

TABLE 3

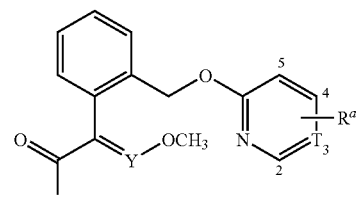

IV

| No. | V | Y | T | $R^a$ | Reference |
|---|---|---|---|---|---|
| IV-1 | OCH$_3$ | CH | N | 2-OCH$_3$, 4-CF$_3$ | WO 96/16047 |
| IV-2 | OCH$_3$ | CH | N | 2-OCH(CH$_3$)$_2$, 4-CF$_3$ | WO 96/16047 |
| IV-3 | OCH$_3$ | CH | CH | 2-CF$_3$ | EP-A 278 595 |
| IV-4 | OCH$_3$ | CH | CH | 4-CF$_3$ | EP-A 278 595 |
| IV-5 | NHCH$_3$ | N | CH | 2-Cl | EP-A 398 692 |
| IV-6 | NHCH$_3$ | N | CH | 2-CF$_3$ | EP-A 398 692 |
| IV-7 | NHCH$_3$ | N | CH | 2-CF$_3$, 4-Cl | EP-A 398 692 |
| IV-8 | NHCH$_3$ | N | CH | 2-Cl, 4-CF$_3$ | EP-A 398 692 |

TABLE 4

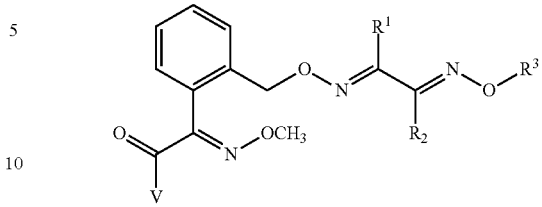

| No. | V | Y | R¹ | B | Reference |
|---|---|---|---|---|---|
| V-1 | $OCH_3$ | CH | $CH_3$ | $(3-CF_3)C_6H_4$ | EP-A 370 629 |
| V-2 | $OCH_3$ | CH | $CH_3$ | $(3,5-Cl_2)C_6H_3$ | EP-A 370 629 |
| V-3 | $NHCH_3$ | N | $CH_3$ | $(3-CF_3)C_6H_4$ | WO 92/13830 |
| V-4 | $NHCH_3$ | N | $CH_3$ | $(3-OCF_3)C_6H_4$ | WO 92/13830 |
| V-5 | $OCH_3$ | N | $CH_3$ | $(3-OCF_3)C_6H_4$ | EP-A 460 575 |
| V-6 | $OCH_3$ | N | $CH_3$ | $(3-CF_3)C_6H_4$ | EP-A 460 575 |
| V-7 | $OCH_3$ | N | $CH_3$ | $(3,4-Cl_2)C_6H_3$ | EP-A 460 575 |
| V-8 | $OCH_3$ | N | $CH_3$ | $(3,5-Cl_2)C_6H_3$ | EP-A 463 488 |
| V-9 | $OCH_3$ | CH | $CH_3$ | $CH=CH-(4-Cl)C_6H_4$ | EP-A 936 213 |

TABLE 5

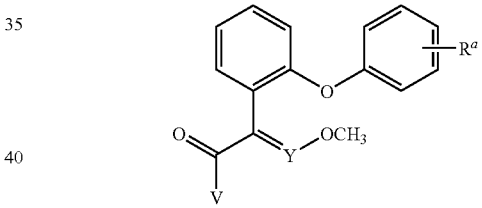

| No. | V | R¹ | R² | R³ | Reference |
|---|---|---|---|---|---|
| VI-1 | $OCH_3$ | $CH_3$ | $CH_3$ | $CH_3$ | WO 95/18789 |
| VI-2 | $OCH_3$ | $CH_3$ | $CH(CH_3)_2$ | $CH_3$ | WO 95/18789 |
| VI-3 | $OCH_3$ | $CH_3$ | $CH_2CH_3$ | $CH_3$ | WO 95/18789 |
| VI-4 | $NHCH_3$ | $CH_3$ | $CH_3$ | $CH_3$ | WO 95/18789 |
| VI-5 | $NHCH_3$ | $CH_3$ | $4-F-C_6H_4$ | $CH_3$ | WO 95/18789 |
| VI-6 | $NHCH_3$ | $CH_3$ | $4-Cl-C_6H_4$ | $CH_3$ | WO 95/18789 |
| VI-7 | $NHCH_3$ | $CH_3$ | $2,4-C_6H_3$ | $CH_3$ | WO 95/18789 |
| VI-8 | $NHCH_3$ | Cl | $4-F-C_6H_4$ | $CH_3$ | WO 98/38857 |
| VI-9 | $NHCH_3$ | Cl | $4-Cl-C_6H_4$ | $CH_2CH_3$ | WO 98/38857 |
| VI-10 | $NHCH_3$ | $CH_3$ | $CH_2C(=CH_2)CH_3$ | $CH_3$ | WO 97/05103 |
| VI-11 | $NHCH_3$ | $CH_3$ | $CH=C(CH_3)_2$ | $CH_3$ | WO 97/05103 |
| VI-12 | $NHCH_3$ | $CH_3$ | $CH=C(CH_3)_2$ | $CH_2CH_3$ | WO 97/05103 |
| VI-13 | $NHCH_3$ | $CH_3$ | $CH=C(CH_3)CH_2CH_3$ | $CH_3$ | WO 97/05103 |
| VI-14 | $NHCH_3$ | $CH_3$ | $O-CH(CH_3)_2$ | $CH_3$ | WO 97/06133 |
| VI-15 | $NHCH_3$ | $CH_3$ | $O-CH_2CH(CH_3)_2$ | $CH_3$ | WO 97/06133 |
| VI-16 | $NHCH_3$ | $CH_3$ | $C(CH_3)=NOCH_3$ | $CH_3$ | WO 97/15552 |

TABLE 6

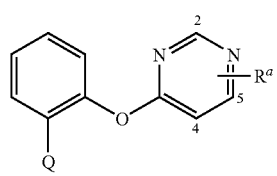

| No. | V | Y | $R^a$ | Reference |
|---|---|---|---|---|
| VII-1 | $NHCH_3$ | N | H | EP-A 398 692 |
| VII-2 | $NHCH_3$ | N | $3-CH_3$ | EP-A 398 692 |
| VII-3 | $NHCH_3$ | N | $2-NO_2$ | EP-A 398 692 |
| VII-4 | $NHCH_3$ | N | $4-NO_2$ | EP-A 398 692 |
| VII-5 | $NHCH_3$ | N | 4-Cl | EP-A 398 692 |
| VII-6 | $NHCH_3$ | N | 4-Br | EP-A 398 692 |

TABLE 7

VII

| No. | Q | $R^a$ | Reference |
|---|---|---|---|
| VIII-1 | $C(=CH-OCH_3)COOCH_3$ | $5-O-(2-CN-C_6H_4)$ | EP-A 382 375 |
| VIII-2 | $C(=CH-OCH_3)COOCH_3$ | $5-O-(2-Cl-C_6H_4)$ | EP-A 382 375 |
| VIII-3 | $C(=CH-OCH_3)COOCH_3$ | $5-O-(2-CH_3-C_6H_4)$ | EP-A 382 375 |

TABLE 7-continued

VII

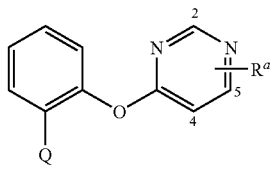

| No. | Q | $R^a$ | Reference |
|---|---|---|---|
| VIII-4 | C(=N—OCH$_3$)CONHCH$_3$ | 5-O-(2-Cl—C$_6$H$_4$) | GB-A 2253624 |
| VIII-5 | C(=N—OCH$_3$)CONHCH$_3$ | 5-O-(2,4-Cl$_2$—C$_6$H$_3$) | GB-A 2253624 |
| VIII-6 | C(=N—OCH$_3$)CONHCH$_{33}$ | 5-O-(2-CH$_3$—C$_6$H$_4$) | GB-A 2253624 |
| VIII-7 | C(=N—OCH$_3$)CONHCH$_3$ | 5-O-(2-CH$_3$,3-Cl—C$_6$H$_3$) | GB-A 2253624 |
| VIII-8 | C(=N—OCH$_3$)CONHCH$_3$ | 4-F, 5-O-(2-CH$_3$—C$_6$H$_4$) | WO 98/21189 |
| VIII-9 | C(=N—OCH$_3$)CONHCH$_3$ | 4-F, 5-O-(2-Cl—C$_6$H$_4$) | WO 98/21189 |
| VIII-10 | C(=N—OCH$_3$)CONHCH$_3$ | 4-F, 5-O-(2-CH$_3$,3-Cl—C$_6$H$_3$) | WO 98/21189 |
| VIII-11 | Q1 | 4-F, 5-O-(2-Cl—C$_6$H$_4$) | WO 97/27189 |
| VIII-12 | Q1 | 4-F, 5-O-(2-CH$_3$,3-Cl—C$_6$H$_3$) | WO 97/27189 |
| VIII-13 | Q1 | 4-F, 5-O-(2,4-Cl$_2$—C$_6$H$_3$) | WO 97/27189 |

Especially preferred are the strobilurins: Compound II-5 (pyraclostrobin), III-1 (kresoxim-methyl), III-3 (dimoxystrobin), III-11 (ZJ 0712), IV-3 (picoxystrobin), V-6 (trifloxystrobin), V-9 (enestroburin), VI-16 (orysastrobin), VII-1 (metominostrobin), VIII-1 (azoxystrobin), and VIII-11 (fluoxastrobin). Particularly preferred is pyraclostrobin (compound II-5), kresoxim-methyl (compound III-1) or azoxystrobin (compound VIII-1), in particular pyraclostrobin.

According to the present invention, for combating Esca, the above described compounds, particularly the strobilurins and preferred strobilurins, can also be used together with other active ingredients, for example with herbicides, pest control agents (such as insecticides and acaricides), growth regulators, fungicides and fertilizers. When mixing the compounds used according to the present invention, particularly a strobilurin as described above, or the compositions comprising them, with one or more such further active ingredients, in particular fungicides, in many cases an expansion of the fungicidal spectrum of activity is achieved and/or the development of pathogen tolerances can be avoided. In many cases, synergistic effects are achieved.

Thus, in a further aspect, the present invention provides the use of at least one compound that inhibits the mitochondrial breathing chain at the level of the b/c$_1$ complex, particularly a strobilurin as defined above, together with at least one further active ingredient, particularly a fungicide, for combating Esca. Particularly, the invention provides the use of a fungicidal composition, comprising at least one compound that inhibits the mitochondrial breathing chain at the level of the b/c$_1$ complex, particularly a strobilurin as defined above, optionally together with at least one further active ingredient, particularly a fungicide, and at least one solid or liquid carrier for combating Esca.

Preferably, the at least one further active ingredient is selected from the group consisting of carboxylic acid amides, azoles, nitrogen-containing heterocyclic compounds, carbamates, dithiocarbamates and other fungicides selected from dodine, iminoctadine, guazatine, kasugamycin, polyoxine, streptomycin, validamycin A, fentin salts, isoprothiolane, dithianon, edifenphos, fosetyl, fosetyl-aluminium, iprobenfos, pyrazophos, tolclofos-methyl, phosphoric acid and the salts thereof, thiophanate methyl, chlorothalonil, dichlofluanid, tolylfluanid, flusulfamide, phthalide, hexachlorobenzene, pencycuron, quintozene, binapacryl, dinocap, dinobuton, bordeaux mixture, copper acetate, copper hydroxide, copper oxychloride, basic copper sulfate, sulfur, spiroxamine, cyflufenamide, cymoxanile and metrafenone.

More preferred, the at least one further active ingredient is selected from the following list of fungicides:

Carboxylic Amides carboxylic acid anilides: benalaxyl, benalaxyl-M, benodanil, bixafen, boscalid, carboxin, mepronil, fenfuram, fenhexamid, flutolanil, furametpyr, metalaxyl, ofurace, oxadixyl, oxycarboxin, penthiopyrad, thifluzamid, tiadinil, 2-amino-4-methyl-thiazole-5-carboxylic acid anilide, 2-chloro-N-(1,1,3-trimethyl-indan-4-yl)-nicotinamide, 4-difluoromethyl-2-methyl-thiazol-5-carboxylic acid-(4'-bromobiphenyl-2-yl)-amide, 4-difluoromethyl-2-methyl-thiazol-5-carboxylic acid-(4'-trifluoromethyl-biphenyl-2-yl)-amide, 4-difluoromethyl-2-methyl-thiazol-5-carboxylic acid-(4'-chloro-3'-fluoro-biphenyl-2-yl)-amide, 3-difluoromethyl-1-methyl-pyrazol-4-carboxylic acid-(3',4'-dichloro-4-fluoro-biphenyl-2-yl)-amide, N-(3',4'-dichloro-5-fluoro-biphenyl-2-yl)-3-difluoromethyl-1-methyl-1H-pyrazole-4-carboxylic acid amide, N-(2-(1,3-dimethyl-butyl)-phenyl)-1,3,3-trimethyl-5-fluoro-1H-pyrazole-4-carboxylic acid amide, N-(4'-chloro-3',5-difluoro-biphenyl-2-yl)-3-difluoromethyl-1-methyl-1H-pyrazole-4-carboxylic acid amide, N-(4'-chloro-3',5-difluoro-biphenyl-2-yl)-3-trifluoromethyl-1-methyl-1H-pyrazole-4-carboxylic acid amide, N-(3',4'-dichloro-5-fluoro-biphenyl-2-yl)-3-trifluoromethyl-1-methyl-1H-pyrazole-4-carboxylic acid amide, N-(3',5-difluoro-4'-methyl-biphenyl-2-yl)-3-difluoromethyl-1-methyl-1H-pyrazole-4-carboxylic acid amide, N-(3',5-difluoro-4'-methyl-biphenyl-2-yl)-3-trifluoromethyl-1-methyl-1H-pyrazole-4-carboxylic acid amide, N-(2-bicyclopropyl-2-yl-phenyl)-3-difluoromethyl-1-methyl-1H-pyrazole-4-carboxylic acid amide, N-(cis-2-bicyclopropyl-2-yl-phenyl)-3-difluoromethyl-1-methyl-1H-pyrazole-4-carboxylic acid amide, N-(trans-2-bicyclopropyl-2-yl-phenyl)-3-difluoromethyl-1-methyl-1H-pyrazole-4-carboxylic acid amide, 3,4-dichloro-isothiazol-5-carboxylic acid-(2-cyano-phenyl)-amide;

carboxylic acid morpholides: dimethomorph, flumorph;

benzoic acid amides: flumetover, fluopicolide (picobenzamid), fluopyram, zoxamide, N-(3-Ethyl-3,5-5-trimethyl-cyclohexyl)-3-formylamino-2-hydroxybenzamide;

other carboxylic acid amides: carpropamide, diclocymet, mandipropamid, oxytetracyclin, silthiofam, N-(6-methoxy-pyridin-3-yl)cyclopropanecarboxylic acid amide, N-(2-(4-[3-(4-chloro-phenyl)-prop-2-inyloxy]-3-methoxy-phenyl)-ethyl)-2-methanesulfonylamino-3-methyl-butyramid, N-(2-(4-[3-(4-chloro-phenyl)-prop-2-inyloxy]-3-methoxy-phenyl)-ethyl)-2-ethanesulfonylamino-3-methyl-butyramide;

Azoles triazoles: azaconazole, bitertanole, bromuconazole, cyproconazole, difenoconazole, diniconazole, diniconazole-M, enilconazole, epoxiconazole, fenbuconazole, flusilazole, fluquinconazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimenol, triadimefon, triticonazole, uniconazole, 1-(4-chloro-phenyl)-2-([1,2,4]triazol-1-yl)-cycloheptanol;

imidazoles: cyazofamid, imazalil, imazalil-sulphate, pefurazoate, prochloraz, triflumizol;

benzimidazole: benomyl, carbendazim, fuberidazole, thiabendazole;

others: ethaboxam, etridiazole, hymexazole;

Nitrogen-Containing Heterocyclic Compounds pyridines: fluazinam, pyrifenox, 3-[5-(4-chloro-phenyl)-2,3-dimethyl-isoxazolidin-3-yl]-pyridine, 2,3,5,6-Tetrachloro-4-methanesulfonyl-pyridine,3,4,5-Trichloropyridine-2,6-dicarbonitrile, N-(1-(5-Bromo-3-chloropyridin-2-yl)-ethyl)-2,4-dichloro-nicotinamide, N-((5-Bromo-3-chloro-pyridin-2-yl)-methyl)-2,4-dichloronicotinamide;

pyrimidines: bupirimat, cyprodinil, diflumetorim, ferimzon, fenarimol, mepanipyrim, nitrapyrin, nuarimol, pyrimethanil;

piperazines: triforin;

pyrroles: fludioxonil, fenpiclonil;

morpholines: aldimorph, dodemorph, dodemorph-acetate, fenpropimorph, tridemorph;

dicarboximide: fluoroimide, iprodion, procymidon, vinclozolin;

others: acibenzolar-S-methyl, anilazin, blasticin-S, captan, chinomethionate, captafol, dazomet, debacarb, diclomezine, difenzoquat, difenzoquat methyl sulphate, fenoxanil, folpet, oxolinic acid, piperalin, fenpropidin, famoxadone, fenamidone, octhilinon, probenazol, proquinazid, pyroquilon, quinoxyfen, tricyclazol, 5-chloro-7-(4-methylpiperidine-1-yl)-6-(2,4,6-trifluorophenyl)-[1,2,4]triazolo[1,5-a]pyrimidine, 2-butoxy-6-iodo-3-propyl-chromen-4-one, 3-(3-bromo-6-fluoro-2-methyl-indole-1-sulfonyl)-[1,2,4]triazole-1-sulfonic acid dimethyllamide;

Carbamates and Dithiocarbamates dithiocarbamates: ferbam, mancozeb, maneb, metiram, metam, methasulphocarb, propineb, thiram, zineb, ziram;

carbamates: diethofencarb, flubenthiavalicarb, iprovalicarb, propamocarb, propamocarb hydrochloride, 3-(4-chloro-phenyl)-3-(2-isopropoxycarbonylamino-3-methyl-butyrylamino)-propionic acid methylester, N-(1-(1-(4-cyanophenyl)ethanesulfonyl)-but-2-yl) carbamic acid-(4-fluorophenyl)ester;

Other Fungicides guanidines: dodine, dodine free base, iminoctadine, iminoctadine-triacetate, iminoctadine-tris(albesilate), guazatine, guazatine-acetate;

antibiotics: kasugamycin, kasugamycin-hydrochloride-hydrate, polyoxine, streptomycin, validamycin A;

organometallic compounds: fentin salts, e.g. fentin acetate, fentin chloride, fentin hydroxide;

sulfur-containing heterocyclic compounds: isoprothiolan, dithianon;

organophosphorous compounds: edifenphos, fosetyl, fosetyl-aluminium, iprobenfos, pyrazophos, tolclofos-methyl, phosphoric acid and the salts thereof;

organo-chloro compounds: thiophanate methyl, chlorothalonil, dichlofluanid, dichlorophen, tolylfluanid, flusulfamid, phthalide, hexachlorbenzene, pencycuron, pentachlorophenole and salts, quintozen, N-(4-chloro-2-nitro-phenyl)-N-ethyl-4-methyl-benzenesulfonamide;

nitrophenyl derivatives: binapacryl, dinocap, dinobuton, dicloran, nitrothalisopropyl, tecnazen;

inorganic active ingredients: Bordeaux mixture, copper acetate, copper hydroxyide, copper oxychloride, basic copper sulfate, sulfur;

others: spiroxamine, cyflufenamide, cymoxanil, metrafenone, biphenyl, bronopol, diphenylamine, mildiomycin, oxin-copper, prohexadione calcium, Tolylfluanid, N—(Cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethylphenyl)-N-ethyl-N-methyl formamidine, N'-(4-(4-fluoro-3-trifluoromethyl-phenoxy)-2, 5-dimethyl-phenyl)-N-ethyl-N-methyl formamidine, N'-(2-methyl-5-trifluormethyl-4-(3-trimethylsilanyl-propoxy)-phenyl)-N-ethyl-N-methyl formamidine, difluormethyl-2-methyl-4-(3-trimethylsilanyl-propoxy)-phenyl)-N-ethyl-N-methyl formamidine.

More preferably, the at least one further fungicide is selected from nitrogen-containing heterocyclic compounds, carbamates, dithiocarbamates and morpholines, in particular selected from diethofencarb, flubenthiavalicarb, iprovalicarb, propamocarb, 3-(4-chlorophenyl)-3-(2-isopropoxycarbonylamino-3-methyl-butyrylamino)-propionic acid methyl ester, N-(1-(1-(4-cyanophenyl/ethanesulfonyl)-but-2-yl) carbamic acid-(4-fluorophenyl)ester, ferbam, mancozeb, maneb, metiram, metam, propineb, thiram, zineb, ziram, aldimorph, dodemorph, fenpropimorph, tridemorph and folpet, especially preferred are metiram, fenpropimorph and folpet.

In one preferred embodiment of the present invention, a two-component composition is used for combating Esca, which comprises one of the strobilurins as defined above together with one active ingredient selected from the further fungicide compounds as defined above. In another preferred embodiment of the present invention, a three-component composition is used for combating Esca, which comprises one strobilurin as defined above together with two active ingredients selected from the further fungicide compounds as defined above. Particularly preferably used are such mixtures, wherein the strobilurin is selected from the preferred strobilurins as outlined above, preferably Pyraclostrobin.

According to one embodiment of the present invention, it is preferred to use a strobilurin selected from pyraclostrobin, kresoxim-methyl, dimoxystrobin, picoxystrobin, trifloxystrobin, enestroburin, orysastrobin, metominostrobin, azoxystrobin, and fluoxastrobin together with one or two further active ingredients as defined above, wherein pyraclostrobin is a particularly preferred strobilurin compound. Specific examples of preferred two-component compositions used according to the present invention comprise pyraclostrobin and metiram, azoxystrobin and metiram, kresoxim-methyl and metiram, pyraclostrobin and folpet, azoxystrobin and folpet, kresoxim-methyl and folpet.

According to the present invention, the compounds detailed above are useful for combating Esca in different kinds of vines. Examples for vine varieties are white vines and red vines, for example Müller-Thurgau, Bacchus, Riesling, Scheurebe, Silvaner and Dornfelder, Lemberger, Tempranillo, Trollinger, respectively.

The vinegrapes can be treated before infection takes place, for example three weeks to one week before the expected Esca attack, i.e. the treatment is protective. During such timeframe, one to 10 applications, more specifically one, two, three, four or five applications during one season are preferably carried out. A markedly reduced susceptibility of the plant to Esca diseases is observed. In another embodiment, the vinegrapes are treated curatively, i.e. when the vinegrapes are already attacked by the fungi, wherein preferably one, two, three, four or five applications during one season are carried out.

In one preferred embodiment of the present invention the method according to the invention is preferably carried out as foliar application or spray application, respectively. Preferably, one, two, three, four, five and up to ten applications during one season are carried out, specifically more than two applications, and up to 10 applications. Also preferred more than two applications, and up to 5 applications during a season are carried out.

One specific application mode is the injection of the compound that inhibits the mitochondrial breathing chain at the level of the $b/c_1$ complex, particularly the strobilurin or the composition containing a strobilurin as defined above, into the vines, preferably directly into the trunks. Usually, the active ingredients are present in the form of a formulation that can be easily injected into the vines.

According to a further embodiment of the present invention, the compound/s or compositions are used by applying the same to the roots of the vines, particularly by application of the active ingredients/formulation to the soil surrounding the roots. The soil near to the plants is preferably treated with one, two or three, specifically two or three applications of the active ingredients and active ingredient formulations, respectively, during one season.

The application rates are usually between 0.01 and 2.0 kg, preferably up to 1.0 kg of active ingredient per hectare.

The compounds used according to the present invention, particularly compounds I, can be converted into the formulations conventionally used for fungicides, for example solutions, emulsions, suspensions, dusts, powders, pastes and granules. The use form depends on the particular purpose; in any case, it should ensure fine and uniform distribution of the compound according to the invention.

Best results are obtained when a formulation is used which supports the transport of the active compounds into the plants, and the distribution within the entire plant.

The formulations can be prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172, 714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example Dichlorophen and enzylalkoholhemiformal.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound(s). In this case, the active compound(s) are employed in a purity of from 90% to 100% by weight, preferably 95% to 100% by weight (according to NMR spectrum).

The compounds used according to the present invention, particularly the strobilurins, or mixtures containing the same as defined above can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compound(s) used according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The active compound may also be used successfully in the ultra-low-volume process (ULV), it being possible to apply formulations comprising over 95% by weight of active compound, or even to apply the active compound without additives.

The following are examples of formulations:
1. Products for dilution with water for foliar applications.
A) Water-soluble concentrates (SL, LS)
   10 parts by weight of the active compound(s) are dissolved in 90 parts by weight of water or a water-soluble solvent. As an alternative, wetters or other auxiliaries are added. The active compound(s) dissolves upon dilution with water, whereby a formulation with 10% (w/w) of active compound(s) is obtained.
B) Dispersible concentrates (DC)
   20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.
C) Emulsifiable concentrates (EC)
   15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.
D) Emulsions (EW, EO, ES)
   25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.
E) Suspensions (SC, OD, FS)
   In an agitated ball mill, 20 parts by weight of the active compound(s) are comminuted with addition of 10 parts by weight of dispersants, wetters and 70 parts by weight of water or of an organic solvent to give a fine active compound(s) suspension. Dilution with water gives a stable suspension of the active compound(s), whereby a formulation with 20% (w/w) of active compound(s) is obtained.
F) Water-dispersible granules and water-soluble granules (WG, SG)
   50 parts by weight of the active compound(s) are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-dispersible powders and water-soluble powders (WP, SP, SS, WS)

75 parts by weight of the active compound(s) are ground in a rotor-stator mill with addition of 25 parts by weight of dispersants, wetters and silica gel. Dilution with water gives a stable dispersion or solution of the active compound(s), whereby a formulation with 75% (w/w) of active compound(s) is obtained.

2. Products to be applied undiluted for foliar applications.

I) Dustable powders (DP, DS)

5 parts by weight of the active compound(s) are ground finely and mixed intimately with 95 parts by weight of finely divided kaolin. This gives a dustable product having 5% (w/w) of active compound(s)

J) Granules (GR, FG, GG, MG)

0.5 part by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

K) ULV solutions (UL)

10 parts by weight of the active compound(s) are dissolved in 90 parts by weight of an organic solvent, for example xylene. This gives a product having 10% (w/w) of active compound(s), which is applied undiluted for foliar use.

The note mentioning the effect of an active compound that inhibits the mitochondrial breathing chain at the level of the $b/c_1$ complex, specifically of a strobilurin or the mixtures containing such compounds for combating Esca may be present as a label on the packaging or in product data sheets. The note may also be present in the case of preparations which can be used in combination with the active ingredients.

The activity of compounds that inhibit the mitochondrial breathing chain at the level of the $b/c_1$ complex, particularly of strobilurins and mixtures containing at least one such compound and at least one further active ingredient against Esca was demonstrated by the following experiments:

EXAMPLES

Use Example 1

Field Trial

1 Material, Methods and Test Conditions

The trials were done on a full production vineyard with the presence of the disease symptoms in the previous years, placed in Requena (Valencia, Spain), using the variety Tempranillo grafted on 110-Ritcher, 25 years old, in an espalier formation, with dripping irrigation and a plantation frame of 2.5×2.5 m that means 1600 vines/ha.

The recorded environmental conditions during the trial were taken from the meteorological station of 'El Cerrito'-Requena (Valencia), obtaining the data on temperature (° C.) and rainfall (mm) (see Table A).

According to the spread symptoms of the disease the trial was set on bands (blocks divided on four subplots of 20 vines each), with a surface per block of 500 m² (80 vines), with the intention to have a great number of vines with symptoms.

The spraying equipment was a hydraulic sprayer model "Maruyama", with a tube of 50 m, nozzle of ceramic disc of 1 mm diameter and a working pressure of 20 bars.

The moment of application was decided according to the vineyard growth stage evolution (see Table A) and the use of preventative criteria of fight against Esca, according the existing sap movement in the vine along its crop cicle, being these moments the most active for the above mentioned fungus.

A fungicidal mixture of Pyraclostrobin (compound II-5) with metiram (5%+55%), applied at a dose rate of 0.2% (0.2 kg of commercially available formulation (tradename: Cabrio Top®, a WG of BASF Aktiengesellschaft) per 100 l water) in a program of four treatments was used in the trials. An untreated plot was used as a control. The active compounds used were applied as commercially available formulations.

The applications were carried out in the different growth stages A, B, C and D (see table A).

TABLE A

| month | Growth stages of vines | BBCH Coding for growth stage (application moment) | Environmental conditions during application |
|---|---|---|---|
| March | lethargy: winter buds | 00 (A) | 800 l water/ha <1 m/s wind speed temperature 14° C. humidity 73% |
| May | inflorescence, clearly visible | 51-53 (B) | 1000 l water/ha <1 m/s wind speed temperature 24° C. humidity 65% |
| June | fruit setting, the young fruits begin to swallow | 71-73 (C) | 1000 l water/ha <1 m/s wind speed temperature 22° C. humidity 75% |
| August | beginning of grapes ripening (change of colour) | 81-83 (D) | 1000 l water/ha <1 m/s wind speed temperature 25° C. humidity 66% |

BBCH-Coding: Compendium of Growth Stage Identification Keys for Mono- and Dicotyledoneus Plants; Autumn 1994, compiled by Reinhold Stauss, Ciba Geigy AG, Postfach, CH-4002 Basel.

2 Results 2.1 Selectivity 7 to 14 days after each application, the selectivity was recorded visually. No injuries of the vines were observed, i.e. there were not observed any phytotoxicity symptoms resuiting from the inventive application of the above active ingredient formulation.

2.2 Efficacy

The efficacy of the treatment was assessed by observing the frequency and the intensity of Esca attack. All the elemental plots were assessed by evaluating all the shoots per vine according a non linear scale of 5 classes, see Table B

TABLE B

| Scale for the different kinds of shoots that were tested | |
|---|---|
| class | description |
| 1 | healthy shoot |
| 2 | shoot with 1-25% of visible injuries |
| 3 | shoot with 26-50% of visible injuries |
| 4 | shoot with >50% of visible injuries |
| 5 | dry shoot | a) Frequency of Esca Attack

TABLE C

| | frequency of Esca attack | | | | | | | | |
|---|---|---|---|---|---|---|---|---|---|
| | % frequency of attack growth stage | | | | transformed data[1] | | | | |
| | A | B | C | D | A | B | C | D | average |
| control | 40.31 | 50.0 | 56.52 | 62.73 | 39.41 | 45.0 | 48.75 | 52.37 | 46.38 a[2] |
| invention | 16.39 | 10.88 | 10.67 | 11.71 | 23.88 | 19.26 | 19.07 | 20.01 | 20.55 b |

[1]data transformed by arcsen√(X/100)
[2]the figures followed by the same letter are not significantly different according to LSD test (P = 0.05)

b) Intensity of Esca Attack

TABLE D

| | intensity of Esca attack | | | | | | | | |
|---|---|---|---|---|---|---|---|---|---|
| | % intensity of attack growth stage | | | | transformed data[1] | | | | |
| | A | B | C | D | A | B | C | D | average |
| control | 18.99 | 22.79 | 21.96 | 37.95 | 25.83 | 28.51 | 27.91 | 38.03 | 30.08 a[2] |
| invention | 8.40 | 2.72 | 2.67 | 4.73 | 16.85 | 9.49 | 9.40 | 12.56 | 12.07 b |

[1]data transformed by arcsen√(X/100)
[2]the figures followed by the same letter are not significantly different according to LSD test (P = 0.05)

The assessment of the frequency and the intensity of Esca attack showed that the treatment according the present invention resulted in a surprisingly effective control of the disease compared to the control plants (95% difference between the vines treated according to the present invention and the control vines). Furthermore, there were not observed any phytotoxicity symptoms using the inventive method for combating Esca.

Use Example 2

Microtitre Test to Evaluate the Efficacy of Fungicides Against *Phaeoacremonium aleophilum* and *Phaeomoniella chlamydospora*, two Fungi of the Esca-Complex The products were provided as technical quality active ingredient. Stock solutions of the active ingredients were prepared in DMSO at a concentration of 10 000 ppm a.i. All products were tested at 125, 31, 8, 2, 0.5 and 0.125 ppm a.i.; the DMSO concentration was the same in all dilutions.

Spore suspensions of the test fungi were prepared in a yeast extract, Bacto peptone and glycerol liquid medium.

Equal volumes of test compound and spore suspension were added, in triplicate, to the wells of 96-well microtitre plates. The optical densities of the wells were measured with the aid of a photometer at 405 nm immediately after preparation.

Incubation of the plates followed at 23° C. Further optical density measurements were made after 7 and 14 days' incubation. Growth in the treated wells was compared with the growth in the control (=water) wells.

In this test, the inhibition of the growth of *Phaeomoniella chlamydospora* was strong to very strong by active compounds kresoxim-methyl, and pyraclostrobin, resp.; and the inhibition of the growth of *Phaeoacremonium aleophilum* was strong to very strong inhibited by active compound pyraclostrobin.

Use Example 3

Efficacy of Pyraclostrobin Against the Growth of Mycelium of Different Pathogens Associated with Esca in Grapes Test pathogens were *Phaeoacremonium* sp., *Phaemoniella chlamydospora* and *Fomitiporella vitis* (pathogens associated with the Esca disease) as well as *Cylindrocarpon destructans* and *Botryosphaeria* sp. (pathogens frequently isolated from vine wood with Esca symptoms).

In this experiment 5 mm diameter disks obtained from pure cultures of the fungi were deposited at the centre of 90 mm Petri dishes containing a solution of potato dextrose agar (PDA) to which different concentrations of pyraclostrobin were added (three repetitions).

Pyraclostrobin was used as Comet®, a commercial formulation of BASF Aktiengesellschaft containing 250 g/l pyraclostrobin. Pyraclostrobin was applied in concentrations of 0, 0.1, 1, 10, 100, and 1000 ppm active ingredient. The concentrations of active ingredient added to the culture medium were determined previously by diffusion of the product in agar inoculated for the corresponding species.

Subsequently the diameters of the pathogen growths (mm) were determined visually until the test material (pathogen in PDA medium without fungicide) fully colonised the Petri dishes. This growth was compared with that obtained from the different concentrations of pyraclostrobin, determining the effectiveness of the fungicide as the proportion between the diameter achieved by the test substance (without application of fungicide product) and the growth diameter of the fungus at a particular concentration.

The level of inhibition of mycelium growth of the different pathogens for pyraclostrobin are as follows:

Levels of inhibition of mycelium growth for different fungal species in relation to fungicide concentration. The results are expressed as percentages and represent the mean of 3 repetitions Percentage mycelium inhibition: pyraclostrobin

| | Conc. [ppm] | | | | | |
|---|---|---|---|---|---|---|
| | 0 | 0.1 | 1 | 10 | 100 | 1000 |
| *Botryosphaeria* sp. | 0.00 | 23.14 | 48.04 | 66.08 | 88.43 | 100.00 |
| *Ganoderma* sp. | 0.00 | 21.18 | 65.88 | 91.37 | 100.00 | 100.00 |
| *Fomitiporella vitis* | 0.00 | 46.47 | 92.75 | 98.62 | 100.00 | 100.00 |
| *Cylindrocarpon destructans* | 0.00 | 33.33 | 69.61 | 86.67 | 90.59 | 100.00 |
| *Phaeoacremonium* sp. | 0.00 | 35.65 | 61.00 | 77.27 | 88.28 | 100.00 |
| *Phaeomoniella chlamydospora* | 0.00 | 64.91 | 93.57 | 95.32 | 96.49 | 100.00 |

This experiment shows that pyraclostrobin provided a good activity on all tested pathogens associated with the esca disease in grapes.

The invention claimed is:

1. A method for combating ESCA comprising contacting the fungi, their habitat, the plants, the soil, and/or materials to be kept free therefrom with an effective amount of a strobilurin selected from the group consisting of pyraclostrobin, trifloxystrobin, orysastrobin, and azoxystrobin which inhibits the mitochondrial breathing chain at the level of the b/c1 complex for combatting Esca.

2. The method of claim 1, wherein the active compound is a strobilurin compound selected from azoxystrobin, pyraclostrobin, and trifloxystrobin.

3. The method of claim 1, wherein the strobilurin compound is pyraclostrobin.

4. The method of claim 1, wherein the strobilurin is used together with at least one further active ingredient.

5. The method of claim 4, wherein the at least one further active ingredient is selected from metiram, fenpropimorph and folpet.

6. The method of claim 1, wherein the strobilurin is azoxystrobin.

7. The method of claim 1, wherein the strobilurin is trifloxystrobin.

* * * * *